US010856963B2

(12) United States Patent
Zhang et al.

(10) Patent No.: US 10,856,963 B2
(45) Date of Patent: Dec. 8, 2020

(54) INFERIOR VENA CAVA FILTER OF BIDIRECTIONAL CONTROLLED PLACEMENT

(71) Applicant: Hangzhou Wei Qiang Medical Technology Co., Ltd., Zhejiang (CN)

(72) Inventors: Tingchao Zhang, Zhejiang (CN); Yang Li, Zhejiang (CN)

(73) Assignee: HANGZHOU WEI QIANG MEDICAL TECHNOLOGY CO., LTD., Hangzhou (CN)

( * ) Notice: Subject to any disclaimer, the term of this patent is extended or adjusted under 35 U.S.C. 154(b) by 117 days.

(21) Appl. No.: 16/303,072

(22) PCT Filed: Mar. 21, 2018

(86) PCT No.: PCT/CN2018/079698
§ 371 (c)(1),
(2) Date: Nov. 19, 2018

(87) PCT Pub. No.: WO2018/188456
PCT Pub. Date: Oct. 18, 2018

(65) Prior Publication Data
US 2019/0216588 A1     Jul. 18, 2019

(30) Foreign Application Priority Data

Apr. 11, 2017 (CN) .......................... 2017 1 0233723

(51) Int. Cl.
*A61F 2/01*     (2006.01)

(52) U.S. Cl.
CPC ........... *A61F 2/01* (2013.01); *A61F 2002/016* (2013.01); *A61F 2230/005* (2013.01); *A61F 2230/0093* (2013.01)

(58) Field of Classification Search
CPC ........................................................ A61F 2/01
See application file for complete search history.

(56) References Cited

U.S. PATENT DOCUMENTS 5,836,968 A * 11/1998 Simon ..................... A61F 2/01
606/200
5,836,969 A    11/1998 Kim et al.
(Continued)

FOREIGN PATENT DOCUMENTS

CN      102811679 A      12/2012
CN      203815661 U       9/2014
(Continued)

OTHER PUBLICATIONS

International search report issued in corresponding international application No. PCT/CN2018/079698 dated Jun. 19, 2018.
(Continued)

*Primary Examiner* — Richard G Louis
(74) *Attorney, Agent, or Firm* — Hauptman Ham, LLP

(57) ABSTRACT

An inferior vena cava filter capable of bidirectional controlled placement is provided. The inferior vena cava filter includes a filter portion and a support portion. The filter portion is configured as a mesh-like structure of a plurality of struts cross-linked. The support portion includes a first support portion and a second support portion disposed on opposite sides of the filter portion, and the first support portion and the second support portion have openings extending in opposite directions. The first support portion extends outwardly radially with respect to a center point of the inferior vena cava filter in a positive direction and then curls inwardly radially in a reverse direction.

19 Claims, 6 Drawing Sheets

(56) References Cited

U.S. PATENT DOCUMENTS

2004/0186510 A1* 9/2004 Weaver .................... A61F 2/01
 606/200
2008/0188887 A1 8/2008 Batiste
2014/0107694 A1 4/2014 Wang
2014/0277077 A1* 9/2014 Roorda .................... A61F 2/01
 606/200

FOREIGN PATENT DOCUMENTS

| CN | 205339216 U | 6/2016 |
| CN | 206007410 U | 3/2017 |
| CN | 107307921 A | 11/2017 |
| CN | 207575293 U | 7/2018 |
| EP | 252236 A1 | 11/2010 |
| EP | 2708206 A1 | 3/2014 |

OTHER PUBLICATIONS

First Search dated Feb. 14, 2019 from corresponding application No. CN 201710233723.X.
Office Action from corresponding application No. CN 201710233723.X.
Extended European Search report issued in corresponding European Application No. 18784622.5 dated Apr. 29, 2019.

* cited by examiner

INFERIOR VENA CAVA FILTER OF BIDIRECTIONAL CONTROLLED PLACEMENT

RELATED APPLICATIONS

The present application is a National Phase of International Application Number PCT/CN2018/079698, filed Mar. 21, 2018, and claims the priority of China Application No. 201710233723.X, filed Apr. 11, 2017.

TECHNICAL FIELD

The present disclosure belongs to the technical field of medical devices and relates to a filter, and particularly relates to a bidirectional controlled placement inferior vena cava filter.

BACKGROUND

Pulmonary embolism (PE) is a common health problem and becomes an important factor leading to death in all age groups. Most pulmonary embolisms result from deep vein thrombosis (DVT) of the lower extremities or the pelvis. Blood clots of the deep vein thrombosis may flow back into the heart through the veins and then into the lung, thus causing pulmonary infarction due to loss of a portion supply of blood and oxygen to the lung.

In current treatment regimens, the use of filters can prevent and reduce the occurrence of pulmonary embolism in the presence of anticoagulant contraindications or anticoagulation ineffectiveness. The filter is generally delivered through the femoral vein to the inferior vena cava. However, when there exists floating thrombi in the bilateral iliac vein or the inferior vena cava, the filter needs to be implanted through the jugular vein or through the antecubital vein, through the superior vena cava, sequentially through the right atrium, and ultimately into the inferior vena cava. Therefore, an ideal inferior vena cava filter can be implanted and retrieved through the femoral vein, and can also be implanted and retrieved through the jugular vein, that is, the placements of the filter into the blood vessel through the jugular vein and through the femoral vein are controllable. The reason for adopting the bidirectional controlled placement inferior vena cava filter is that, when the filter needs to be implanted into a specific part of the inferior vena cava in surgery, the position of the filter placed may not meet the requirements due to misoperation or other reasons, thus it is required to retrieve the filter into a sheath, and then reposition and replace the filter. In the related art, only unidirectional controlled placement of the filter can be supported. While the filter is implanted to flow in another direction, the filter is pushed out directly from the sheath, where a controlled placement of the filter is not supported. In this case, if the position of the filter placed does not meet the requirements, it is unable to retrieve the filter and the position of the filter can not be adjusted.

In the related art, a cage-shaped inferior vena cava filter is used for filtering thrombi. The cage-shaped inferior vena cava filter has the following disadvantages. The filter is only capable of unidirectional controlled placement through the femoral vein, and when the filter is placed through the jugular vein, the filter is unable to be retrieved into the sheath and replaced after being pushed out from the sheath. In addition, the filter is provided with a vertical rod along an axial direction, and the entire vertical rod is in close contact with the blood vessel wall after the filter is implanted into the blood vessel. After a period of time, the vascular intima climbs and completely covers the vertical rod, such that the filter must be retrieved within the period of time when the intima has not yet climbed and covered the vertical rod. The filter needs to be retrieved in a short period of time and cannot meet the needs of most clinical applications. Furthermore, since the filter is provided with a retrieval hook at the protruding point of the cage-shaped structure, in a case that the filter is tilted, the retrieval hook is closely attached to the blood vessel wall, such that the retrieval hook is unable to hook over a trap of a catcher, resulting in an inability to retrieve the filter, thus the filter will remain permanently in the patient's body and become a foreign body.

In the related art, there is another common inferior vena cava filter provided with struts in a conical shape. The funnel-like filter utilizing this configuration is implanted into the inferior vena cava to filter thrombi, and an opening of the funnel-like filter should be directed toward the blood flow so as to effectively intercept the thrombi. When the funnel-like filter is inversely placed into the inferior vena cava, the filter will act as an inverted cone-shaped. According to fluid dynamics, the blood flow velocity is fast in the central region of the blood vessel while slow near the blood vessel wall, such that the thrombi generally flow with the blood in the central region of the blood vessel. The blood in the central region produces a shunting effect when encounters a conical tip of the filter, such that the thrombi approach the blood vessel wall with blood flow. For the cone-shape filter provided with struts, the struts are more densely arranged toward the conical tip, and more sparsely arranged toward the end of the filter, thus filter holes close to the vessel wall are sparser such that the thrombi are not easily intercepted. Therefore, this filter cannot be inversely placed. The above-mentioned filter has the following disadvantages. Due to the directivity of the conical structure, the filter can only be controllably placed through the jugular vein, and when placed through the femoral vein, the filter is unable to be retrieved into the sheath and replaced after pushed out from the sheath. In addition, since the retrieval hook of the filter is disposed at a tip end of the cone, in a case that the filter is tilted, the retrieval hook at the tip end will be closely attached to the blood vessel wall, thereby the filter is not easily to be retrieved by the catcher.

SUMMARY

The technical problem to be solved by the present disclosure is that the filter in the related art is in an inability to support bidirectional controlled placement, the filter is not easily to be captured and retrieved when the filter is tilted, and the filter is not easily to be retrieved when the vascular intima has climbed and covered the filter. The present disclosure provides a bidirectional controlled placement inferior vena cava filter which can be implanted and retrieved through the femoral vein and through the jugular vein. The filter has good thrombus filtering effect, can be implanted for a longer period of time, and is easier to be captured and retrieved.

The technical solution adopted by the present disclosure to solve the above-mentioned technical problem is described as follows.

An inferior vena cava filter capable of bidirectional controlled placement is provided. The inferior vena cava filter includes a filter portion and a support portion. The filter portion is configured as a mesh-like structure of a plurality of struts cross-linked. The support portion includes a first support portion and a second support portion disposed on opposite sides of the filter portion, and the first support portion and the second support portion have openings extending in opposite directions. The first support portion extends outwardly radially with respect to a center point of the inferior vena cava filter in a positive direction and then curls inwardly radially in a reverse direction. The second support portion extends outwardly radially with respect to the center point in the positive direction.

According to one embodiment of the inferior vena cava filter capable of bidirectional controlled placement, the first support portion and the second support portion are supported on a blood vessel wall by point contact.

According to one embodiment of the inferior vena cava filter capable of bidirectional controlled placement, the plurality of struts of the filter portion are cross-linked and form cross-linked nodes.

According to one embodiment of the inferior vena cava filter capable of bidirectional controlled placement, the first support portion, the second support portion, and the filter portion are configured as an integral structure. The first support portion includes a plurality of first support struts extending outwardly from the cross-linked nodes of the filter portion and then curling inwardly in the reverse direction. The second support portion includes a plurality of second support struts extending outwardly from the cross-linked nodes of the filter in the positive direction.

Alternatively, the first support portion, the second support portion, and the filter portion are configured as a separate assembly structure. One of the first support portion and the second support portion is configured as a separate structure, and another one is configured as an integral structure with the filter portion. The first support portion of the separate structure includes a plurality of first support struts extending outwardly from the center point in the positive direction and then curling inwardly in the reverse direction. The second support portion of the separate structure includes a plurality of second support struts extending outwardly from the center point in the positive direction.

Alternatively, the first support portion, the second support portion, and the filter portion are configured as a separate assembly structure. The first support portion, the second support portion, and the filter portion are configured as separate structures and fixedly connected together. The first support portion includes a plurality of first support struts extending outwardly from the center point in the positive direction and then curling inwardly in the reverse direction. The second support portion includes a plurality of second support struts extending outwardly from the center point in the positive direction. The filter portion is configured as a structure of the plurality of struts cross-linked in a funnel shape, a hollow mesh spherical shape, a mesh disc shape, or a mesh plate shape.

According to one embodiment of the inferior vena cava filter capable of bidirectional controlled placement, the first support struts or the second support struts, and the struts of the filter portion are staggered along a central axis of the inferior vena cava filter. Alternatively, at least one of the first support strut and the second support strut is formed integrally with the strut of the filter portion, and the first support struts and the second support struts are staggered along the central axis.

According to one embodiment of the inferior vena cava filter capable of bidirectional controlled placement, the first support portion includes at least three first support struts arranged symmetrically about a central axis of the inferior vena cava filter, the at least three first support struts extends outwardly in the positive direction and then curls inwardly in the reverse direction to form a support structure with a collection space, the at least three first support struts is supported on the blood vessel wall by point contact. The second support portion includes at least three second support struts arranged symmetrically about the central axis, the at least three second support struts extends outward in the positive direction to form a support structure with a collection space, the at least three second support struts is supported on the blood vessel wall by point contact.

According to one embodiment of the inferior vena cava filter capable of bidirectional controlled placement, at least one of the first support strut and the second support strut includes an anchoring portion configured to anchor in the inner vessel wall.

According to one embodiment of the inferior vena cava filter capable of bidirectional controlled placement, the second support struts are configured as curved struts or straights struts extending outwardly.

According to one embodiment of the inferior vena cava filter capable of bidirectional controlled placement, an end of the first support strut or a tangent of the end of the first support strut, and a central axis of the first support portion define an angel therebetween, and the angle is greater than or equal to 180°. A maximum outer diameter of the first support portion is substantially coincident with an inner diameter of the blood vessel such that the first support struts are supported on the inner vessel wall by point contact.

According to one embodiment of the inferior vena cava filter capable of bidirectional controlled placement, each of the first support struts includes a first support segment and a second support segment extending in sequence outwardly radially with respect to the center point. The first support segment or a tangent of each point of the first support segment, and the central axis of the first support segment define an angle therebetween ranging from zero to 90°. The second support segment or a tangent of each point of the second support segment, and the central axis of the first support segment define an angle being greater than or equal to 90°. An end of second support segment or a tangent of each point of the end of the second support segment, and the central axis of the first support segment define an angle being greater than or equal to 180°. The second support segment or the tangent of each point of the second support segment, and the first support segment define an angle being greater than 90°. The second support segment of the first support strut is supported on the blood vessel wall by point contact.

According to one embodiment of the inferior vena cava filter capable of bidirectional controlled placement, the inferior vena cava filter further includes a retrieval portion connected with at least one of the filter portion and the support portion.

According to the present disclosure, the filter portion configured as the cross-linked mesh-like structure can improve filtering effect of the inferior vena cava filter. The first support portion and the second support portion disposed on opposite sides of the filter portion extend outwardly in the reverse and positive directions respectively, thereby forming a funnel-shaped or cage-shaped structure in the positive and reverse directions. Therefore, the first support portion and the second support portion not only can support the filter on the blood vessel wall, but also have a function of gathering and intercepting thrombi, and the filtering effect is improved.

More importantly, the inferior vena cava filter provided by the present disclosure is capable of bidirectional controlled placement, providing two options for operators and improving controllability of surgery operations. Since the filter provided by the present disclosure has better filtering effects whether it is implanted into the blood vessel in the positive direction or in the reverse direction, the retrieval hook can always be positioned at a side close to the operator whether the filter is implanted through the femoral vein or through the jugular vein. Therefore, when the retrieval hook is connected to a delivery system to implant the filter, a controlled placement function of repeatedly placing and repeatedly retrieval the filter can be implemented.

In addition, since the first support portion and the second support portion are supported on the blood vessel wall by point contact, the filter has a small contact area with the inner vessel wall, such that only a small portion of the filter will be covered by the vascular intima when the vascular intima has climbed and covered the filter. When the filter needs to be retrieved, the struts of the filter can be pulled out from the vascular intima without causing a significant damage to the vascular intima, such that the timing of retrieving the filter can be delayed, thereby expanding the therapeutic time window for a patient.

The filter provided by the present disclosure has two support portions at two positions spaced apart and forms a stable support on the blood vessel wall, such that the filter possesses a better self-centering performance, thereby preventing the filter from tilting, effectively avoiding the retrieval hook from attaching to the inner vessel wall, and facilitating the capture of retrieval hook and the removing of the filter.

BRIEF DESCRIPTION OF THE DRAWINGS

The present disclosure can be further illustrated in conjunction with the accompanying drawings and embodiments.

DETAILED DESCRIPTION OF ILLUSTRATED EMBODIMENTS

To illustrate objectives, technical solutions, and advantageous effects of the disclosure more clearly, the specific embodiments of the present disclosure will be described in detail herein with reference to accompanying drawings.

The directions involved in the embodiments of the present disclosure are defined as follows. For two directions along a central axis of the filter, a positive direction is defined as a direction from a first support portion to a second support portion, and a reverse direction is defined as a direction from the second support portion to the first support portion. The positive direction and the reverse direction are defined with respect to the filter itself and are independent of an orientation of the filter implanted into the blood vessel. In addition, the central axis may refer to a central axis of the filter, and may also refer to a central axis of the first support portion, a filter portion, or the second support portion.

According to a first embodiment of the present disclosure, an inferior vena cava filter capable of bidirectional controlled placement is provided, as illustrated in FIGS. 1 to 5. The inferior vena cava filter includes a filter portion 1400 and a support portion. The filter portion 1400 is configured as a mesh-like structure of multiple struts 1400a cross-linked. The support portion includes a first support portion 1200 and a second support portion 1100 disposed on opposite sides of the filter portion 1400, and the first support portion 1200 and the second support portion 1100 have openings extending in opposite directions. The first support portion 1200 extends outwardly radially with respect to a center point of the inferior vena cava filter in the positive direction and then curls inwardly radially in the reverse direction. The second support portion 1100 extends outwardly radially with respect to the center point in the positive direction.

The filter provided by the present disclosure includes at least three parts, that is, the filter portion 1400, the first portion 1200, and the second portion 1100. The first support portion 1200 and the second support portion 1100 are disposed on opposite sides of the filter portion 1400 and extend in the reverse direction and the positive direction respectively. The filter portion 1400 is configured to filter thrombi. The first support portion 1200 and the second support portion 1100 are configured to support the filter stably on the blood vessel wall 2000, and to collect and gather the thrombi.

Figure 1:
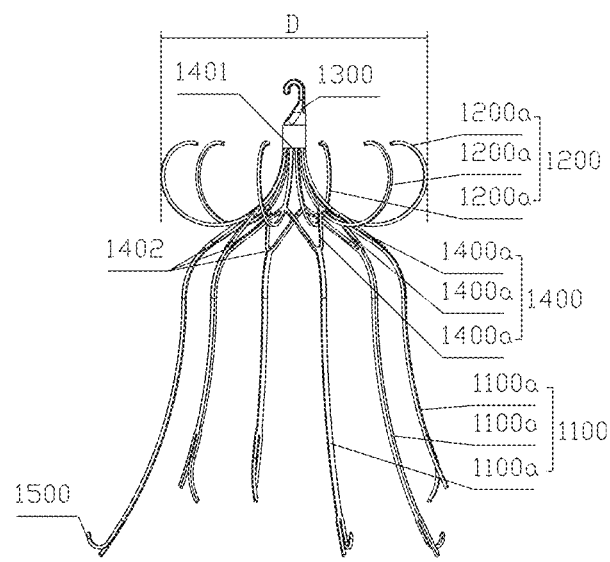
FIG. 1 is a schematic structural view of a filter according to a first embodiment of the present disclosure.
Figure 2:
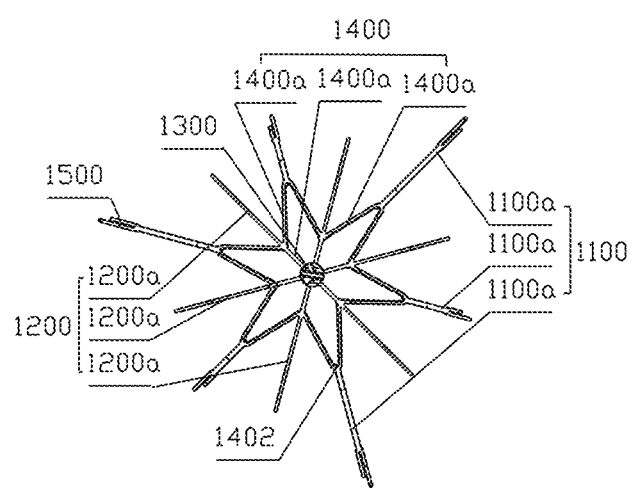
FIG. 2 is a top view of the filter according to the first embodiment of the present disclosure.

As illustrated in FIG. 1 and FIG. 2, when the filter is implanted into the blood vessel, the filter portion 1400 is disposed transversely in the blood vessel and configured to intercept the thrombi. Therefore, a main structure of the filter portion 1400 appears a transversely cross-linked mesh-like structure. The cross-linked structure includes the multiple struts 1400a. The multiple struts 1400a are arranged at a certain distance and then cross-connected at nodes to form a sheet-like structure or extended radially into other shape. The mesh-like structure of the multiple struts cross-linked in the embodiment includes multiple angle-shaped or rhombus-shaped structures formed by cross-linking the multiple struts 1400a extending outwardly radially with respect to the center point of the filter portion 1400. The mesh-like structure is capable of radially collapsed configuration and expanded configuration, and applicable to be received and stored in a sheath. Since most thrombi are agglomerated, the cross-linked structure (such as an angled cross-linked structure, a rhombic cross-linked structure, or the like) enables a better intercept of the thrombi by the filter portion 1400. The multiple struts 1400*a* are cross-linked with each other and cross-linked nodes are formed where the struts 1440*a* are cross-linked. A cross-linked node formed at the center point of the filter portion 1400 is defined as a central cross-linked node 1401, and other cross-linked nodes formed at an outermost side of the filter portion 1400 are defined as terminal cross-linked nodes 1402. Preferably, the filter portion 1400 is an axially symmetric structure centered on the center cross-linking node 1401. The filter portion 1400 includes relatively long struts extending outwardly with respect to the center point of the filter portion 1400 in the positive direction, and further includes relatively short struts transversely connected with the relatively long struts, so as to form the multiple angle-shaped or rhombus-shaped structures. Therefore, the filter portion 1400 is a funnel-shaped structure as a whole with gradually increased diameters. The multiple struts 1400*a* of the filter portion 1400 can be provided as an integral structure, or can be provided as a structure where ends of the multiple struts 1400*a* are respectively welded with each other at the cross-linked nodes. Besides a funnel-shaped structure, the filter portion 1400 can also be in a hollow mesh spherical shape, a mesh disc shape, or a mesh plate shape formed by the multiple struts 1400*a* cross-linked.

A maximum distance defined by the terminal cross-linked nodes 1402 (that is, the cross-linked nodes at the outermost side of the filter portion 1400) is less than the diameter of the blood vessel. Preferably, the maximum distance is less than 16 mm, which can avoid contact between the filter portion 1400 and the blood vessel wall 2000, thereby reducing climbing and covering of the vascular intima and facilitating the retrieval of the filter.

The first support portion 1200 and the second support portion 1100 are supported on the blood vessel wall 2000 by point contact. The first support portion 1200 and the second support portion 1100 disposed on opposite sides of the filter portion 1400 can be made integrally with or formed separately from the filter portion 1400. According to the embodiment, the first support portion 1200 and the second support portion 1100 are made integrally with the filter portion 1400. As illustrated in FIGS. 1 to 4, the first support portion 1200, the second support portion 1100, and the filter portion 1400 are configured as an integral structure. The first support portion 1200 includes multiple first support struts 1200*a* extending outwardly radially from the cross-linked nodes of the filter portion 1400 in the positive direction and then gradually curling inwardly radially in the reverse direction, and the second support portion 1100 includes multiple second support struts 1100*a* gradually extending outwardly from the cross-linked nodes of the filter in the positive direction. In one implementation, the first support portion 1200 extends outwardly from the terminal cross-linked nodes 1402 or from middle cross-linked nodes, and then gradually curls inwardly in the reverse direction. The second support portion 1100 extends outwardly from the terminal cross-linked nodes 1402 in the positive direction, that is, in a direction along which the funnel-shape structure of the filter portion 1400 extends outwardly. The integral structure may be integrally molded, which is formed by laser cutting OD 2.0 mm nickel-titanium tubes and then heat setting by a mold.

The first support portion 1200 can be configured as an axially symmetric structure, which can prevent the filter from tilting and prevent a retrieval hook from attaching to the blood vessel wall 2000. The first support portion 1200 includes at least three first support struts 1200*a* arranged symmetrically about the central axis of the inferior vena cava filter. The at least three first support struts 1200*a* extend outwardly in the positive direction and then gradually curl inwardly in the reverse direction to form a support structure which has a collection space with an opening extending in the reverse direction. The at least three first support struts are supported on the blood vessel wall by point contact, which can reduce climbing and covering of the vascular intima. The first support portion 1200 includes at least three first support struts 1200*a*. In the embodiment of the present disclosure, six first support struts 1200*a* arranged symmetrically about the central axis are adopted.

An end of the first support strut 1200*a* or a tangent of the end of the first support strut, and a central axis of the first support portion 1200 define an angle $\beta$ therebetween, and the angle $\beta$ is greater than or equal to 180°. A maximum outer diameter of the first support portion 1200 is substantially coincident with an inner diameter of the blood vessel such that the first support struts 1200*a* are supported on the inner vessel wall by point contact. It should be noted that the maximum outer diameter refers to the diameter of a circle formed by points of the support struts farthest away from the central axis, that is, the maximum outer diameter is twice a distance between the central axis and a point of the first support struts 1200*a* farthest away from the central axis. During a deploying procedure, the first support struts 1200*a* extend within the blood vessel. When the deploying procedure has been completed, an end of the first support strut 1200*a* or a tangent of the end of the first support strut, and the central axis of the first support portion 1200 define an angel therebetween, and the angle $\beta$ is greater than or equal to 180°, regardless of a structure of the first support strut 1200*a*. Therefore, the end of the first support strut 1200*a* is arranged offset from the blood vessel wall 2000, and at least in parallel with the blood vessel wall 2000, such that the end of the first support strut 1200*a* will not pierce the blood vessel wall 2000.

Figure 5:
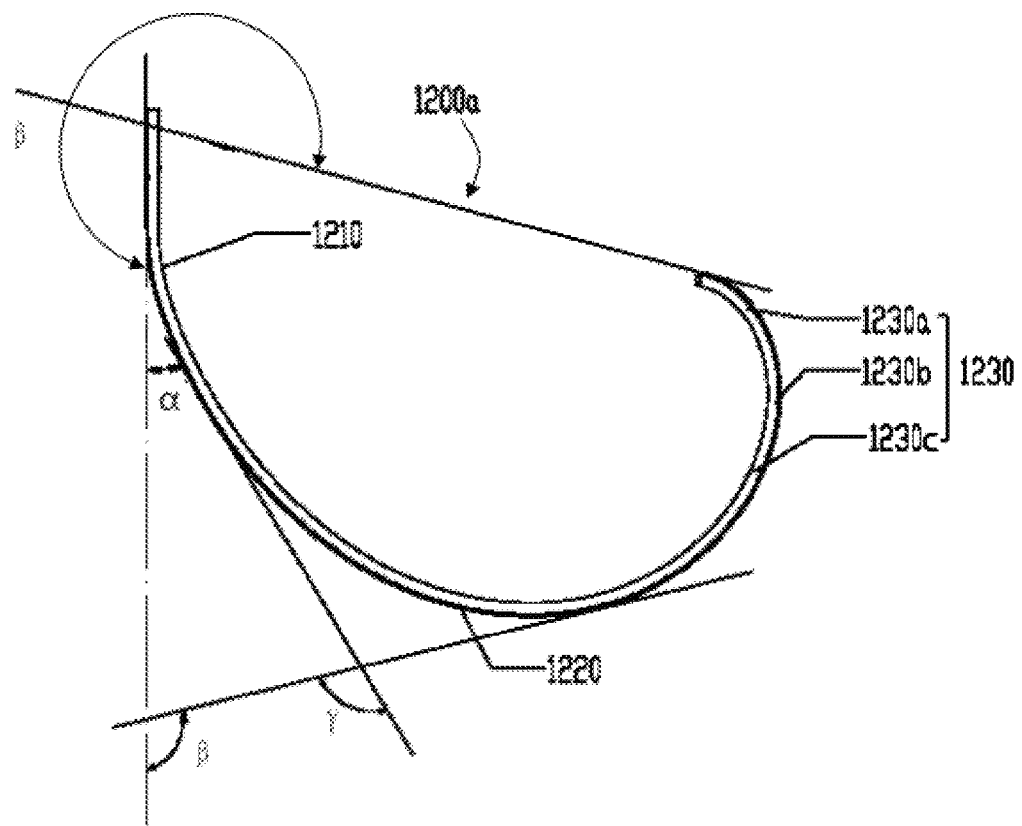
FIG. 5 is a schematic structural view of a first support strut of the filter according to the first embodiment of the present disclosure.

As illustrated in FIG. 5, the structures and functions of portions of the first support strut 1200*a* are different at different positions. Each of the first support struts 1200*a* mainly includes two parts of a first support segment 1210 and a second support segment 1230. The first support segment 1210 and the second support segment 1230 extend in sequence outwardly radially. In one implementation, a transition segment 1220 is provided between the first support segment 1210 and the second support segment 1230. The above-mentioned three segments are configured as different structures with different shapes and lengths. The central axis and one of the first support segment 1210 and a tangent of each point of the first support segment 1210 define an angle $\alpha$ greater than zero and less than 90°. The central axis and one of the second support segment 1230 and a tangent of each point of the second support segment 1230 define an angle $\beta$ greater than 90°. In addition, since the end of each of the first support struts 1200*a* is an end of the second support segment 1230, thus an angle $\beta$ defined by the central axis and one of the end of the second support segment 1230 and a tangent of the end of the second support segment 1230 is greater than or equal to 180°. Such a structure can ensure that after the first support strut 1200*a* is positioned, the end of the first support strut 1200*a* curls an angle greater than 180° before the first support strut 1200*a* attaches to the vessel wall. The ends of multiple first support segments 1210 are assembled with the retrieval portion 1300 and the second support portion 1100, and the second support segment 1230 is disposed as an end portion of the first support strut 1200*a*.

The first support segment 1210 and one of the second support segment 1230 and a tangent of each point of the second support segment 1230 define an angle γ greater than 90°. In one implementation, the first support segment 1210 and one of the second support segment 1230 and a tangent of the second support segment 1230 define an angle γ greater than and equal to 180°, which can ensure that the second support segment 1230 curls in a direction opposite to the filter portion 1400, as illustrated in FIG. 1. The transition segment 1220 is a transition portion between the first support segment 1210 and the second support segment 1230. Therefore, the length and shape of the transition segment 1220 can be determined according to the shapes of the first support segment 1210 and the second support segment 1230, so as to facilitate a smooth transition between the first support segment 1210 and the second support segment 1230, and a corresponding curl effect is achieved. The first support segment 1210, the second support segment 1230, and the transition segment 1220 may be curved bars, straight bars, fold bars, or a mixed arrangement of at least two bars in the above-described shapes. In one implementation, the first support segment 1210, the second support segment 1230, and the transition segment 1220 are curves whose radiuses of curvature continuously changes (that is, the radiuses of curvature gradually reduces).

"Point contact" is a relative concept, meaning that the first support strut 1200a contacts with the blood vessel wall 2000 at a relative small contact area. Compared to the length and diameter of the first support strut 1200, the contact between the first support strut 1200a and the blood vessel wall 2000 can be considered as a kind of point contact. The first support portion 1200 has a maximum outer diameter ranged from 10 mm to 40 mm, and the maximum diameter of the blood vessel is ranged from 16 mm to 34 mm, normally 24 mm.

As illustrated in FIG. 5, the second support segment 1230 of the first support strut 1200a may include a first sub-strut 1230a, a second sub-strut 1230b, and a third sub-strut 1230c. In the embodiments of the present disclosure, the second support segment 1230 is a curve structure. In one implementation, the radius of curvature of the second sub-strut 1230b is less than that of the first sub-strut 1230a. The second sub-strut 1230b and the central axis define an angle β, and a range of the angle β is changed from 90°≤β<180° to β≥180°, thereby forming point contact on the inner vessel wall. In another implementation, the second sub-strut 1230b can be in a curved-line shape or a fold-line shape with a C-shaped or V-shaped opening facing the central axis, and forms a point contact with the inner vessel wall. The first sub-strut 1230a and the third sub-strut 1230c can be in a straight-line shape or a fold-line shape, and the entire second support strut 1230 is bent in the reverse direction of the filter. The second sub-segment 1230b has a relative minimal radius of curvature, and one or multiple furthest points of the second sub-segment 1230b from the central axis are in contact with the inner vessel wall.

As illustrated in FIG. 1 and FIG. 2, the second support portion 1100 includes at least three second support struts 1100a arranged asymmetrically with respect to the central axis. The second support struts 1100a extend outwardly in the positive direction to form a support structure which has a collection space with an opening extending in the positive direction. The second support struts 1100a are supported on the blood vessel wall by point contact. The second support struts 1100a can be configured as a strut structure, cage-shape structure, or the like. For the strut structure, the second support portion 1100 can be configured as a single layer or multi-layer structure. In the embodiment, as illustrated in FIG. 1, the second support portion 1100 is configured as a single layer structure with the multiple second support struts 1100a arranged asymmetrically with respect to the central axis, and the multiple second support struts 1100a have a same shape and structure. The number of the second support struts 1100a can be set as needed, and six second support struts 1100a are adopted in this embodiment. Each of the second support struts 1100a can be configured as a straight strut extending outwardly, or a curved strut with a certain curvature that can reduce a contact area between the second support strut 1100a and the inner vessel wall, thereby avoiding climbing and covering of the vascular intima. In this embodiment, the curved strut adopted is recessed from the middle of the curved strut to the central axis, which can reduce the contact area between the second support strut 1100a and the inner vessel wall. Each of the second support struts 1100a and the central axis define an angle greater than 0° and less than 90°, and the specific size of the angle can be adjusted according to actual needs.

The first support strut 1200a or the second support strut 1100a includes an anchoring portion 1500 for anchoring in the blood vessel wall 2000. In one implementation, the anchoring portion 1500 is disposed on an end of the first support strut 1200a or an end of the second support strut 1100a. The anchoring portion 1500 of the first support strut 1200a is vertical to the central axis, and configured to fix the first support strut 1200a to the blood vessel wall 2000, thereby avoiding excessively deep penetration of the end of the first support strut 1200a into the blood vessel wall 2000. In one implementation, the anchoring portion 1500 of the second support strut 1100a is vertical to the central axis for preventing displacement of the filter in positive or reverse direction. The anchoring portions 1500 of the second support strut 1100a may not positioned in a same plane, so as to reduce entanglement of the anchoring portions 1500.

The retrieval portion 1300 is configured to retrieve the filter. The retrieval portion 1300 is disposed on the center of the first support portion 1200, and fixedly connected together with or formed integrally with the first support portion 1200. The retrieval portion 1300 includes a hook (that is, the retrieval hook) or a hanging ring configured to retrieve the filter into the sheath.

Figure 3:
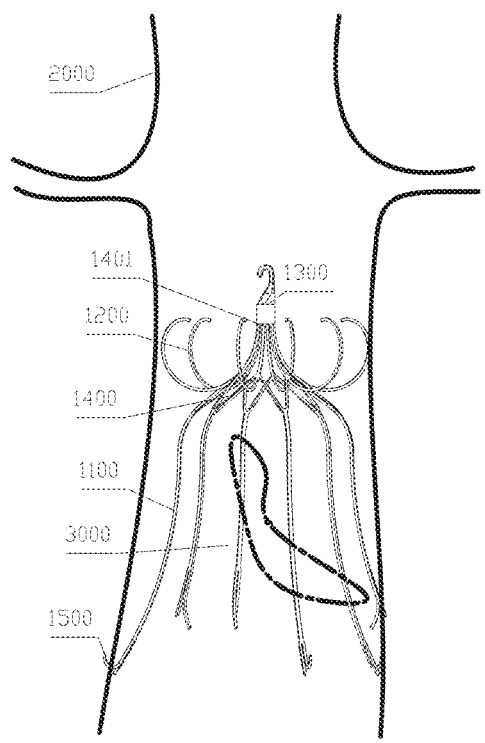
FIG. 3 is a schematic view of an implanting state of the filter implanted in a positive direction according to the first embodiment of the present disclosure.

According to the clinical preoperative evaluation, the appropriate inferior vena cava filter implantation path is selected. FIG. 3 is a schematic diagram illustrating an implanting state of the filter implanted through the jugular vein. In this case, the second support portion 1100 and the filter portion 1400 surround a space to intercept a thrombus 3000. Since the filter portion 1400 is configured as a cross-linked mesh-like structure, it has a good thrombus intercepting effect. The curved-line shape of the second support portion 1100 can maximally prevent the second support struts 1100a from attaching to the inner vessel wall and reduce the climbing and covering of the vascular intima. In addition, the anchoring portion 1500 can prevent displacement of the filter in positive or reverse direction. The first support portion 1200 is supported on the inner vessel wall by point contact, such that the filter has better self-centering performance to prevent the filter from tilting and effectively prevent the retrieval hook from attaching to the inner vessel wall, thereby facilitating the retrieve of the filter. When the filter is required to be retrieved, the retrieval hook of the retrieval portion 1300 can be captured through the jugular vein by a retrieval catheter and a catcher, and the entire filter is retrieved into the sheath and taken out of the body. Compared to the cage-shape filter that is unable to be retrieved through the jugular vein, the filter of the present disclosure has a wider range of applications.

Figure 4:
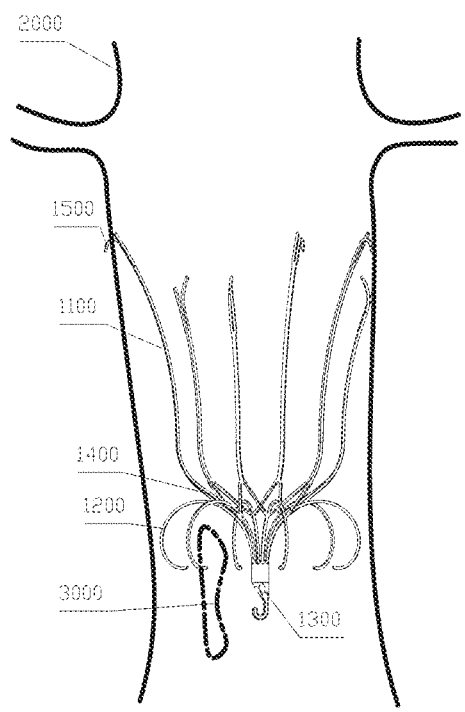
FIG. 4 is a schematic view of an implanting state of the filter implanted in a reverse direction according to the first embodiment of the present disclosure.

FIG. 4 is a schematic diagram illustrating an implanting state of the filter implanted through the femoral vein. In this case, the second support portion 1100 and the filter portion 1400 surround a space to intercept a thrombus 3000. Since the filter portion 1400 is configured as a cross-linked mesh-like structure, it has a good thrombus intercepting effect. The first support portion 1200 is supported on the inner vessel wall by point contact, such that the filter has better self-centering performance to prevent the filter from tilting and effectively prevent the retrieval hook from attaching to the inner vessel wall, thereby facilitating the retrieval of the filter. The curved-line shape of the second support portion 1100 can maximally prevent the second support struts 1100a from attaching to the inner vessel wall and reduce the climbing and covering of the vascular intima. In addition, the anchoring portion 1500 can prevent displacement of the filter in positive or reverse direction. When the filter is required to be retrieved, the retrieval hook of the retrieval portion 1300 can be captured through the femoral vein by a retrieval catheter and a catcher, and the entire filter is retrieved into the sheath and taken out of the body. Compared to a strut-shape filter in the related art that is unable to be retrieved through the femoral vein, the filter of the present disclosure has a wider range of applications.

Figure 6:
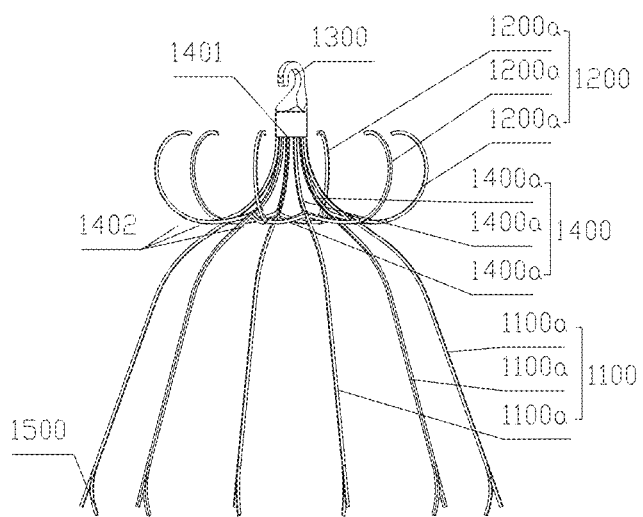
FIG. 6 is a schematic structural view of a filter according to a second embodiment of the present disclosure.
Figure 7:
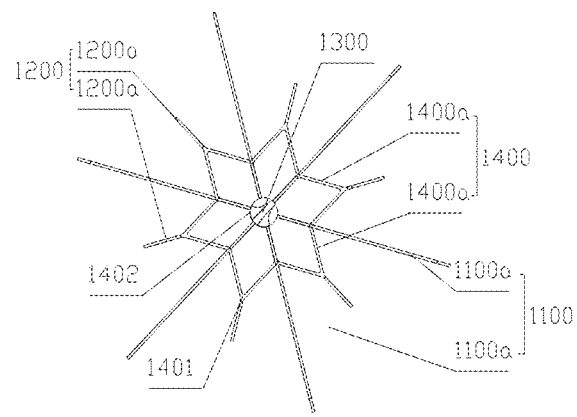
FIG. 7 is a top view of the filter according to the second embodiment of the present disclosure.

In a second embodiment, as illustrated in FIG. 6 and FIG. 7, the filter is improved on the basis of the first embodiment. The difference is that two first support struts 1200a extends from two terminal cross-linking nodes 1402 and then re-combine and curl inwardly radially.

The end of the second support struts 1100a includes an anchoring portion 1500. Each of the second support struts 1100a is configured as a straight strut, thereby preventing entanglement of the anchoring portions 1500.

The structures of the other components of the filter in the second embodiment are the same as that of the first embodiment, which will not be described herein.

Figure 8:
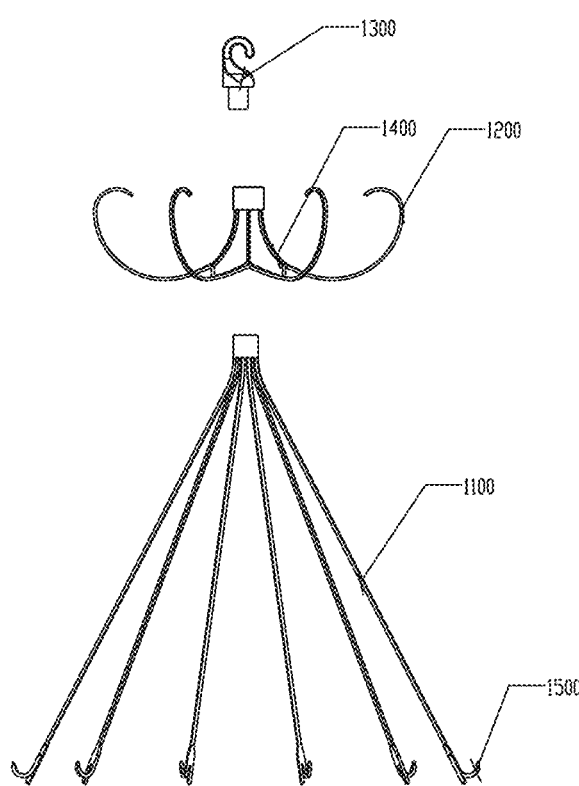
FIG. 8 is a schematic structural view of a filter according to a first implementation of a third embodiment of the present disclosure.
Figure 9:
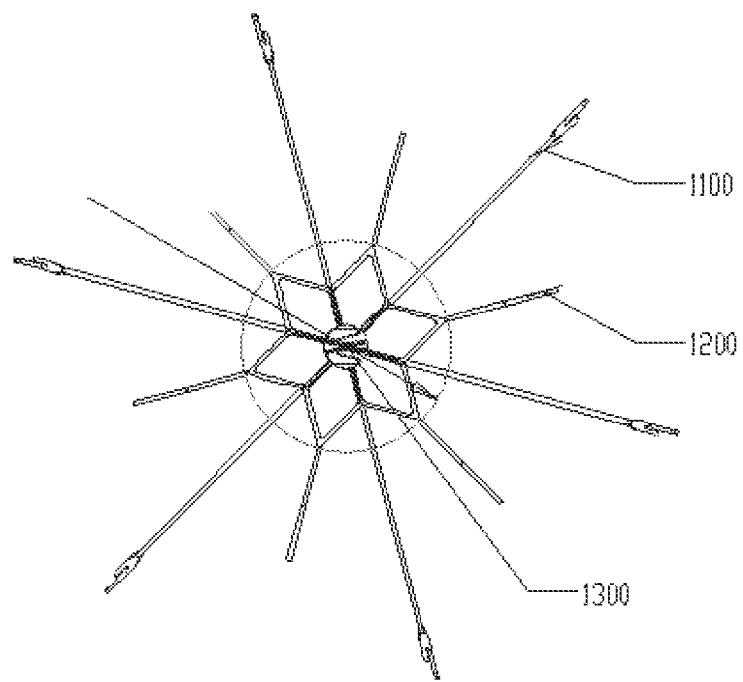
FIG. 9 is a top view of the filter according to the first implementation of the third embodiment of the present disclosure.
Figure 10:
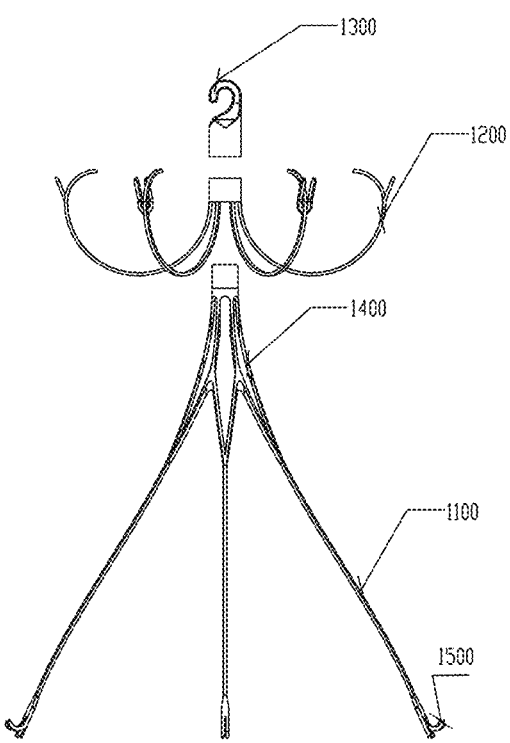
FIG. 10 is a schematic structural view of a filter according to a second implementation of the third embodiment of the present disclosure.
Figure 11:
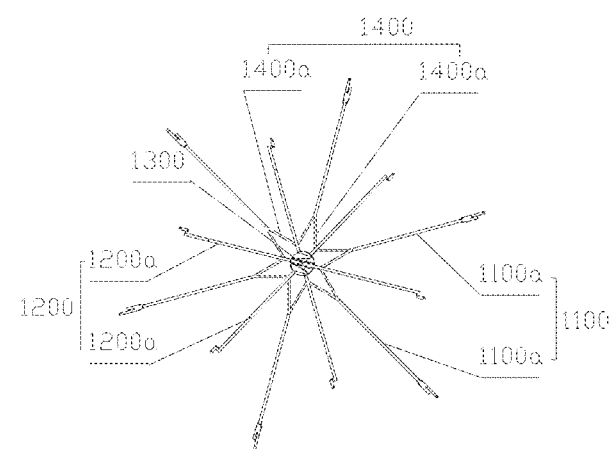
FIG. 11 is a top view of the filter according to the second implementation of the third embodiment of the present disclosure.

In a third embodiment, as illustrated in FIGS. 8 to 11, the first support portion 1200, the second support portion 1100, and the filter portion 1400 are configured as a separate assembly structure. One of the first support portion 1200 and the second support portion 1100 is configured as a separate structure, another one is configured as an integral structure with the filter portion 1400, thereby forming a two-layer filtering structure. Two layers of the structure are molded separately and then welded together. In one implementation, the separate structure includes a first support portion 1200 with multiple first support struts 1200a extending outwardly with respect to the center point in the positive direction and then gradually curling inwardly in the reverse direction. In one implementation, the separate structure includes a second support portion 1100 with multiple second support struts 1100a gradually extending outwardly with respect to the center point. As illustrated in FIGS. 8 to 9, the first support portion 1200 and the filter portion 1400 are configured as an integral structure, and the second support portion 1100 is configured as a separate structure. The second support portion 1100 and the filter portion 1400 are stacked and fixed together to form the two-layer structure. As illustrated in FIGS. 10 to 11, the second support portion 1100 and the filter portion 1400 are configured as an integral structure, and the first support portion 1200 is configured as a separate structure. The first support portion 1200 and the filter portion 1400 are stacked and fixed together to form the two-layer structure.

In one implementation, the first support struts 1200a or the second support struts 1100a, and the struts 1400a of the filter portion 1400 are staggered around the central axis. In one implementation, the first support struts 1200a and the second support struts 1100a respectively form an integral structure with some of the struts 1400a of the filter portion 1400, that is, the first support struts 1200a and some of the struts 1400a are configured as an integral structure, and the second support struts 1100a and some of the struts 1400a are configured as an integral structure. The first support struts 1200a and the second support struts 1100a are staggered around the central axis, which can increase the thrombus filtering effect.

The other structures of the other components of the first support portion 1200, the second support portion 1100, and the filter portion 1400 in the third embodiment are the same as those of the first and the second embodiments, which will not be described herein.

Other than the above-mentioned structure, the separate assembly structure can also be formed as follows. Each of the filter portion 1400, the first support portion 1200 and the second support portion 1100 is configured as a separate structure, and the three separate structures are fixedly connected together to form a three-layer structure. The first support portion 1200 includes multiple first support struts 1200a extending outwardly with respect to the center point in the positive direction and then gradually curling inwardly in the reverse direction. The second support portion 1100 includes multiple second support struts 1100a gradually extending outwardly with respect to the center point in the positive direction. The specific structures of the first support portion 1200, the second support portion 1100, and the filter portion 1400 in the third embodiment are the same as those of the above-mentioned embodiments, which will not be described herein.

The filter portion can be configured as a structure of the plurality of struts cross-linked in a funnel shape, a hollow mesh spherical shape, a mesh disc shape, or a mesh plate shape.

What is claimed is:

1. An inferior vena cava filter, capable of bidirectional controlled placement, comprising:
    a filter portion, configured as a mesh-like structure of a plurality of struts cross-linked; and
    a support portion, comprising a first support portion and a second support portion disposed on opposite sides of the filter portion, and the first support portion and the second support portion having openings extending in opposite directions, wherein
    the plurality of struts of the filter portion are cross-linked and form cross-linked nodes, wherein one of the cross-linked nodes formed at a center point of the filter portion is defined as a central cross-linked node, and other of the cross-linked nodes formed at an outermost side of the filter portion are defined as terminal cross-linked nodes; and
    the first support portion extends outwardly radially from the central cross-linked node in a positive direction and then curls inwardly radially in a reverse direction, and the second support portion extends, from the terminal cross-linked nodes, outwardly radially in the positive direction.

2. The inferior vena cava filter of claim 1, wherein the first support portion and the second support portion are supported on a blood vessel wall by point contact.

3. The inferior vena cava filter of claim 1, wherein the first support portion, the second support portion, and the filter portion are configured as an integral structure; the first support portion comprises a plurality of first support struts extending outwardly from the central cross-linked node of the filter portion and curling inwardly in the reverse direction; the second support portion comprises a plurality of second support struts extending outwardly from the terminal cross-linked nodes of the filter in the positive direction.

4. The inferior vena cava filter of claim 1, wherein the first support portion, the second support portion, and the filter portion are configured as a separate assembly structure; one of the first support portion and the second support portion is configured as a separate structure, and another one is configured as an integral structure with the filter portion; the first support portion of the separate structure comprises a plurality of first support struts; and the second support portion of the separate structure comprises a plurality of second support struts.

5. The inferior vena cava filter of claim 1, wherein the first support portion, the second support portion, and the filter portion are configured as a separate assembly structure; the first support portion, the second support portion, and the filter portion are configured as separate structures and fixedly connected together; the first support portion comprises a plurality of first support struts; the second support portion comprises a plurality of second support struts; and the filter portion is configured as a structure in a funnel shape, a hollow mesh spherical shape, a mesh disc shape, or a mesh plate shape.

6. The inferior vena cava filter of claim 3, wherein
the first support struts or the second support struts, and the struts of the filter portion are staggered along a central axis of the inferior vena cava filter; or
at least one of the first support struts of the plurality of first support struts and at least one of the second support struts of the plurality of second support struts are formed integrally with the strut of the filter portion, and the first support struts and the second support struts being staggered along the central axis.

7. The inferior vena cava filter of claim 3, wherein
the plurality of first support struts of the first support portion comprises at least three first support struts arranged symmetrically about a central axis of the inferior vena cava filter, the at least three first support struts being supported on a blood vessel wall by point contact; and
the plurality of second support struts of the second support portion comprises at least three second support struts arranged symmetrically about the central axis, the at least three second support struts being supported on the blood vessel wall by point contact.

8. The inferior vena cava filter of claim 3, wherein at least one of the first support struts of the plurality of first support struts and the second support struts of the plurality of second support struts comprises an anchoring portion configured to anchor in the inner vessel wall.

9. The inferior vena cava filter of claim 3, wherein the second support struts are configured as curved struts or straights struts.

10. The inferior vena cava filter of claim 3, wherein
an end of at least one of the first support struts of the plurality of first support struts or a tangent of the end of the at least one of the first support struts of the plurality of first support struts, and a central axis of the first support portion define an angel therebetween, and the angle being greater than or equal to 180°; and
a maximum outer diameter of the first support portion is substantially coincident with an inner diameter of the blood vessel such that the first support struts are supported on the inner vessel wall by point contact.

11. The vena cava filter of claim 4, wherein
the plurality of first support struts or the plurality of second support struts, and the struts of the filter portion are staggered along a central axis of the inferior vena cava filter; or
at least one of the first support struts of the plurality of first support struts or at least one of the second support struts of the plurality of second support struts is formed integrally with the strut of the filter portion, and the first support struts and the second support struts being staggered along the central axis.

12. The vena cava filter of claim 4, wherein
the plurality of first support struts of the first support portion comprises at least three first support struts arranged symmetrically about a central axis of the inferior vena cava filter, the at least three first support struts being supported on a blood vessel wall by point contact; and
the plurality of second support struts of the second support portion comprises at least three second support struts arranged symmetrically about the central axis, the at least three second support struts being supported on the blood vessel wall by point contact.

13. The vena cava filter of claim 4, wherein
an end of at least one of the first support struts of the plurality of first support struts or a tangent of the end of the at least one of first support struts of the plurality of first support struts, and a central axis of the first support portion define an angel therebetween, and the angle being greater than or equal to 180°; and
a maximum outer diameter of the first support portion is substantially coincident with an inner diameter of the blood vessel such that the first support struts are supported on the inner vessel wall by point contact.

14. The vena cava filter of claim 5, wherein
the plurality of first support struts of the first support portion comprises at least three first support struts arranged symmetrically about a central axis of the inferior vena cava filter, the at least three first support struts being supported on a blood vessel wall by point contact; and
the plurality of second support struts of the second support portion comprises at least three second support struts arranged symmetrically about the central axis, the at least three second support struts being supported on the blood vessel wall by point contact.

15. The vena cava filter of claim 5, wherein
an end of at least one of the first support struts of the plurality of first support struts or a tangent of the end of the at least one of first support struts of the plurality of first support struts, and a central axis of the first support portion define an angel therebetween, and the angle being greater than or equal to 180°; and
a maximum outer diameter of the first support portion is substantially coincident with an inner diameter of the blood vessel such that the first support struts are supported on the inner vessel wall by point contact.

16. The inferior vena cava filter of claim 10, wherein
each of the first support struts comprises a first support segment and a second support segment extending in sequence outwardly radially;
the first support segment or a tangent of each point of the first support segment, and the central axis of the first support segment define an angle therebetween ranging from zero to 90°; the second support segment or a tangent of each point of the second support segment, and the central axis of the first support segment define an angle being greater than or equal to 90°; an end of second support segment or a tangent of each point of the end of the second support segment, and the central axis of the first support segment define an angle being greater than or equal to 180°; the second support segment or the tangent of each point of the second support segment, and the first support segment define an angle being greater than 90°; and the second support segment of the first support strut is supported on a blood vessel wall by point contact.

17. The vena cava filter of claim 13, wherein
each of the first support struts comprises a first support segment and a second support segment extending in sequence outwardly radially;
the first support segment or a tangent of each point of the first support segment, and the central axis of the first support segment define an angle therebetween ranging from zero to 90°; the second support segment or a tangent of each point of the second support segment, and the central axis of the first support segment define an angle being greater than or equal to 90°; an end of second support segment or a tangent of each point of the end of the second support segment, and the central axis of the first support segment define an angle being greater than or equal to 180°; the second support segment or the tangent of each point of the second support segment, and the first support segment define an angle being greater than 90°; and the second support segment of the first support strut is supported on a blood vessel wall by point contact.

18. The inferior vena cava filter of claim 3, further comprises a retrieval portion connected with at least one of the filter portion and the support portion.

19. The inferior vena cava filter of claim 1, wherein
the first support portion comprises a plurality of first support struts, and each of the plurality of first support struts has a first support segment, a second support segment, and a transition segment;
the first support segment extends from the central cross-linked node in a direction toward the filter portion;
the transition segment is connected between the first support segment and the second support segment; and
the second support segment extends from the transition segment in a direction away from the filter portion and curls in a direction away from the filter portion toward the central cross-linked node.

\* \* \* \* \*